United States Patent
Weng et al.

(10) Patent No.: US 8,587,440 B2
(45) Date of Patent: Nov. 19, 2013

(54) METHOD AND SYSTEM FOR MONITORING DRIVER

(75) Inventors: Ming-Cong Weng, Changhua County (TW); Yu-Sheng Liao, Changhua County (TW); Yu-Song Chen, Changhua County (TW)

(73) Assignee: Automotive Research & Test Center, Changhua County (TW)

( * ) Notice: Subject to any disclaimer, the term of this patent is extended or adjusted under 35 U.S.C. 154(b) by 678 days.

(21) Appl. No.: 12/704,142

(22) Filed: Feb. 11, 2010

(65) Prior Publication Data

US 2011/0068934 A1 Mar. 24, 2011

(30) Foreign Application Priority Data

Sep. 22, 2009 (TW) .............................. 98131931 A

(51) Int. Cl.
  *G08B 23/00* (2006.01)
  *H04N 9/47* (2006.01)
(52) U.S. Cl.
  USPC ............................................ 340/575; 348/77
(58) Field of Classification Search
  USPC ......................................................... 348/143
  See application file for complete search history.

(56) References Cited

U.S. PATENT DOCUMENTS

| 6,243,015 | B1 | 6/2001 | Yeo |
| 6,496,117 | B2 | 12/2002 | Gutta et al. |
| 6,717,518 | B1 * | 4/2004 | Pirim et al. ................... 340/576 |
| 2003/0151516 | A1 * | 8/2003 | Basir et al. .................... 340/575 |
| 2004/0090334 | A1 * | 5/2004 | Zhang et al. .................. 340/575 |
| 2008/0126281 | A1 * | 5/2008 | Kisacanin et al. ............. 706/20 |

FOREIGN PATENT DOCUMENTS

EP 1901252 A2 3/2008

* cited by examiner

*Primary Examiner* — Brian Zimmerman
*Assistant Examiner* — Cal Eustaquio
(74) *Attorney, Agent, or Firm* — Roesnberg, Klein & Lee

(57) ABSTRACT

A method and system for monitoring a driver is disclosed. Firstly, an inner cabin image of a vehicle's cabin is continuously captured. Next, a face detection of a driver for the inner cabin image is performed to obtain a face detection result. Next, the inner cabin image and the face detection result corresponding to the inner cabin image are stored. When the system observes that either the face of the driver is not detected or the face is not shown within a reasonable face region of at least two continuous inner cabin images according to each face detection result, the system outputs a warning signal to alert the driver. The invention determines a driving state of a driver in a cabin with a method of analyzing a position of a face or a head and using an image extractor having large capture range and a low resolution.

18 Claims, 4 Drawing Sheets

METHOD AND SYSTEM FOR MONITORING DRIVER

BACKGROUND OF THE INVENTION

1. Field of the Invention

The present invention relates to a monitoring technology, particularly to a method and a system for monitoring a driver.

2. Description of the Related Art

Transportation vehicles have become more popular and the number has dramatically increased to the point where traffic accidents frequently occur. Many accidents are due to driver fatigue while driving. Driver fatigue not only causes many traffic accidents but negatively affects the body and mind of a driver. Therefore, avoiding driving fatigue has an important social consequence.

Many kinds of driver detection warning systems work to determine by analyzing the line of vision of a driver or integrating network signals of a car. The U.S. Pat. No. 6,243,015 determines fatigue level of a driver though closing level of eyes (namely, the vertical height of eyes). If the fatigue level of the driver has reached a predetermined level, the system outputs a fatigue warning signal. If the fatigue level of the driver is higher than a predetermined value, the system decreases an accumulating value of the fatigue level.

U.S. Pat. No. 6,496,117 determines whether a driver feels overly tired by analyzing the line of vision of the driver. In other words, if the fatigue level of a driver is determined by the technology of the above-mentioned two patent publications, a computer monitoring hardware apparatus having high cost and high resolution is required. However, an expensive apparatus cannot be justified by everyone during a depressed economy.

In view of the problems and shortcomings of the prior art, the present invention provides a method and a system for monitoring a driver, so as to solve the afore-mentioned problems of the prior art.

SUMMARY OF THE INVENTION

An objective of the present invention is to provide a method and a system for monitoring a driver, which determines a driving state of a driver in a cabin with a method of analyzing a position of a face or a head and using an image extractor having a large capture range and low resolution, so as to reduce the cost of the image extractor and improve the convenience for using the image extractor.

To achieve the abovementioned objective, the present invention provides a method for monitoring a driver comprising steps of capturing an inner cabin image of a cabin or cockpit; performing a face detection of a driver on the inner cabin image to obtain a face detection result; storing the inner cabin image and the face detection result corresponding to the inner cabin image; repeating the above-mentioned steps, and when an accumulating number of the stored inner cabin images reaches a predetermined value, begin executing the following steps; capturing the inner cabin images at a plurality of adjacent storing time points and the corresponding face detection results thereof; determining whether at least one corresponding inner cabin image catches a face of the driver according to each captured face detection result; if yes, begin executing the following steps; and if no, outputting a warning signal to alert said driver; and determining whether said faces of two continuous and corresponding inner cabin images are shown within a reasonable face region according to each captured face detection result; if yes, returning to the step of capturing the inner cabin images at the adjacent storing time points and the corresponding face detection results thereof; and if no, outputting the warning signal to alert the driver.

The present invention also provides a system for monitoring a driver comprising: an image extractor for continuously capturing an inner cabin image; an image signal process unit coupled to the image extractor for performing a face detection of a driver on the inner cabin image to obtain a face detection result. After detecting the face, a nose of the driver is detected to obtain a position of the nose and a head deflection angle. When the face is not shown within a reasonable face region of at least two continuous inner cabin images and the head deflection angle is higher than a predetermined threshold, a control signal is outputted to an alerter, and then the alerter outputs a warning signal to alert the driver.

The present invention can not only determine the head deflection direction of the driver faces toward the front or the side through the information of the face detection result but obtain a more accurate head deflection angle by detecting a position of the nose of the driver. When the head deflection angle is higher than the predetermined threshold, the present invention observes that the line of vision of the driver has diverged from the front direction of the car. Therefore, the warning signal is sent out.

Below, the embodiments are described in detail in cooperation with the drawings to make easily understood the characteristics, technical contents and accomplishments of the present invention.

DETAILED DESCRIPTION OF THE INVENTION

Figure 1:
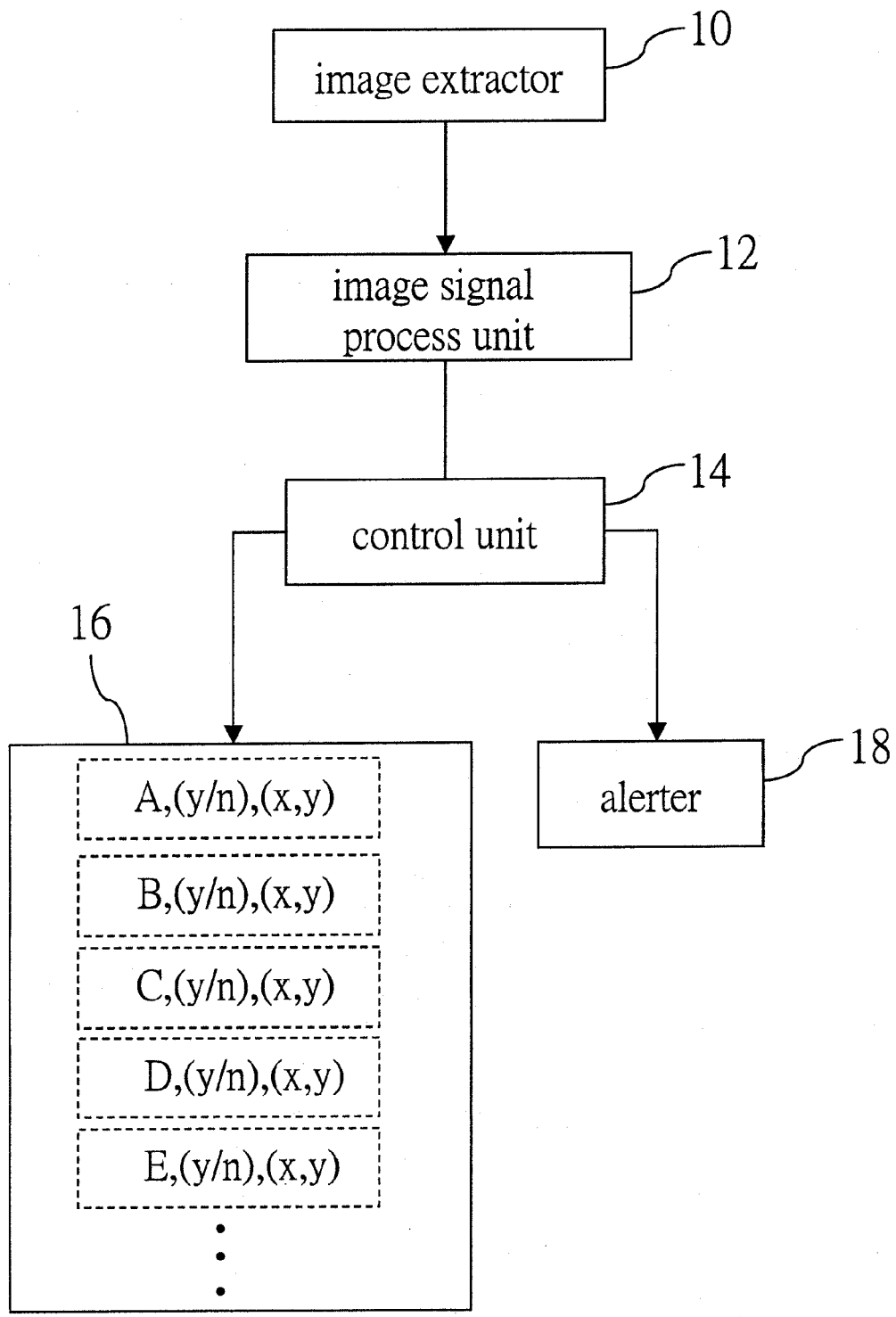
FIG. 1 is a block diagram showing a circuit according to an embodiment of the present invention.

For the safety of a driver in a driving situation, the present invention provides a technology for monitoring a driver. Referring to FIG. 1, the present invention is set up in a cabin or cockpit of a vehicle such as a car. The present invention comprises an image extractor 10, an image signal process unit 12, a control unit 14, a memory 16, and an alert 18, wherein the image extractor 10 is coupled to the image signal process unit 12, and the control unit 14 is coupled to the image signal process unit 12, the memory 16, and the alert 18.

The image extractor 10 is used to continuously capture an inner cabin image of a cabin or cockpit. Besides, the image extractor 10 is disposed near the cabin or cockpit. For example, the image extractor 10 is disposed above an exit of an air conditioner, on a driving mirror, on an instrument panel, on a visor arranged above the left side of the cabin or cockpit, above an instrument panel, or to the left of a pillar of the cabin or cockpit. Because the image extractor 10 is only used to capture the inner cabin image, an image extractor having a large capture range and a low resolution is required to achieve the purpose of the present invention. Thus, the cost of the image extractor is reduced. Also, the method for operating this image extractor is easy enough to improve the convenience for using this image extractor.

The image signal process unit 12 performs the face detection or nose detection of a driver on the inner cabin image by the Adaboost algorithm, so as to obtain a face detection result or a positional coordinate of a nose of the driver respectively. The face detection result comprises a catch result and a positional coordinate of a face of the driver. The catch result of the face reveals the information of catching the face or un-catching the face.

The control unit 14 controls to store the inner cabin image and the corresponding face detection result thereof in the memory 16. Additionally, the control unit 14 captures the inner cabin images and the corresponding face detection results thereof at a plurality of adjacent storing time points from the memory 16, and when the control unit 14 observes that the face is not shown in one corresponding inner cabin image or the face is not shown within a reasonable face region of at least two continuous and corresponding inner cabin images according to each captured face detection result, the control unit 16 outputs a control signal to the alerter 18. Therefore, after receiving the control signal, the alerter 18 outputs a warning signal to alert the driver.

Following are two methods of deciding the position of the reasonable face region. One method is described as the following: the control unit 16 takes the inner cabin images catching the face from the memory 16, and then decides the position of the reasonable face region by the positional coordinate of the face having the highest existing probability. Alternately, the control unit 16 predetermines a squarely-facing face region used as the reasonable face region.

The control unit 14 can perform the determination on a nose of the driver apart from the face. The control unit 14 compares the positional coordinate of the nose with the reasonable face region to obtain the head deflection angle of the driver. When the head deflection angle is higher than or equal to a predetermined threshold, the control unit 14 controls the alerter 18 to output the warning signal, so as to alert the driver.

Figure 2:
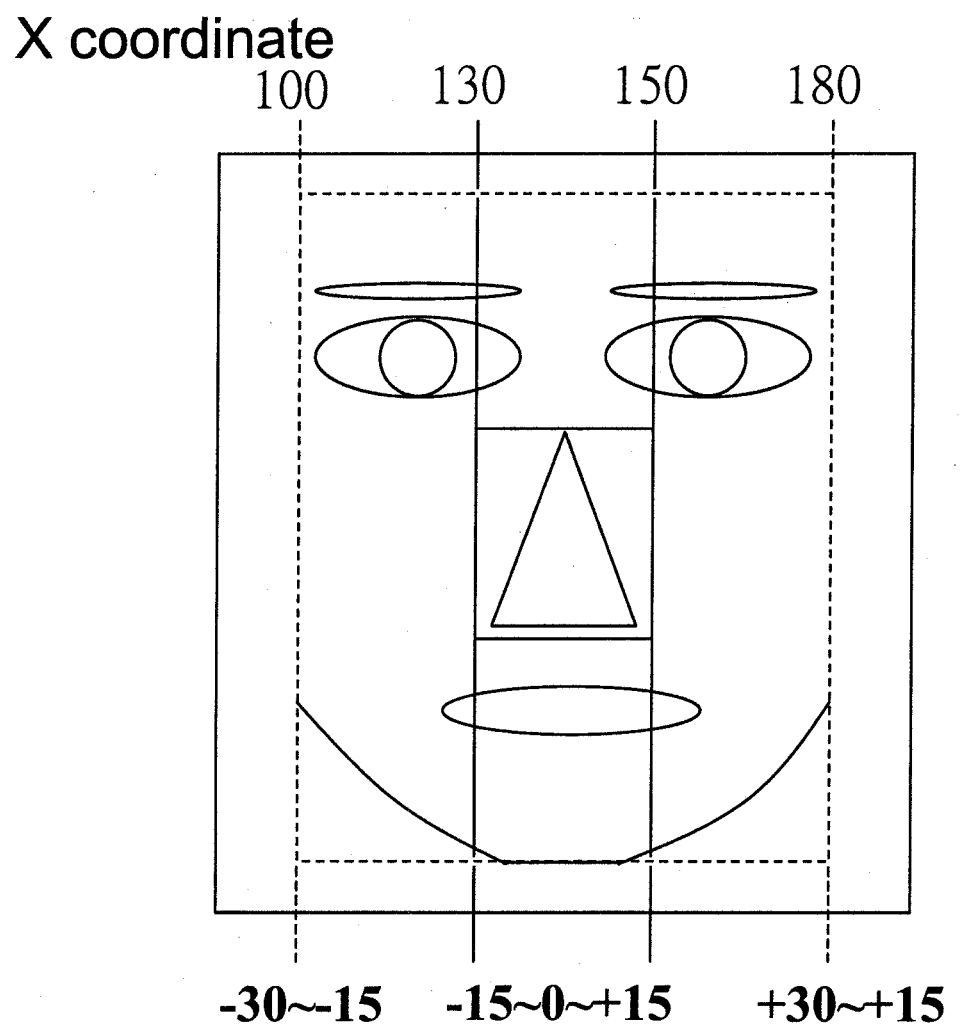
FIG. 2 is a diagram schematically showing a squarely-facing face region according to an embodiment of the present invention

The squarely-facing face region used as the reasonable face region is an example. Moreover, refer to FIG. 2, which shows the squarely-facing face region, wherein the squarely-facing face region has a resolution of 320×240. The position of nose is located on the middle of the squarely-facing face region, whose position is about 50% on the X axis. After estimating the positional coordinate, the positional coordinate of the nose is about 140 on the X axis, and the width of the nose is about 10 with this resolution. In order to get a tolerance range, the positional coordinate of the nose is between 130 and 150 on the X axis of the squarely-facing face region. Additionally, the image signal process unit 12 detects the nose of the driver at the same time. Therefore, when the head of the driver is deflected slightly (−15~−30 degrees), the position of the nose is shifted to 35% on the X axis of the squarely-facing face region. In other words, the positional coordinate of the nose is between 100 and 130 on the X axis. On the contrary, the nose having the poitional coordinate of between 100 and 130 on the X axis infers that the head deflection angle of the driver is between −30 and −15 degrees.

Figure 3:
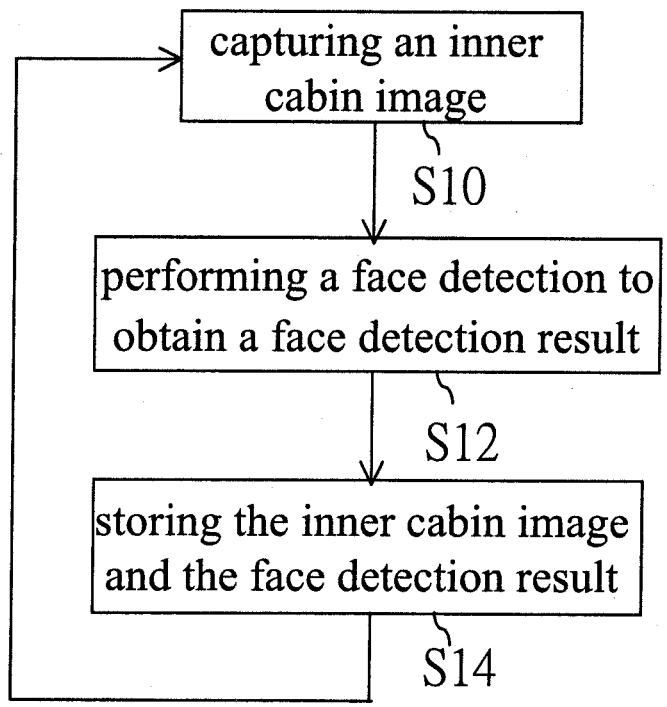
FIG. 3 is a flow chart of a monitoring method according to an embodiment of the present invention.

Refer to FIG. 1 and FIG. 3. Following is a description of the operating process of the present invention. In the beginning, a monitoring method comprising three steps is performed. Firstly, in Step S10, the image extractor 10 captures an inner cabin image of a cabin or cockpit. Next, in Step S12, the image signal process unit 12 performs a face detection of a driver on the inner cabin image to obtain a face detection result by an Adaboost algorithm. The face detection result comprises a catch result and a positional coordinate of a face of the driver. Finally, in Step S14, the control unit 14 stores the inner cabin image and the corresponding face detection result thereof in the memory 16. The process returns to Step S12 after finishing Step S14. In other words, the monitoring method is repeated continuously. Therefore, as time goes on, the memory 16 will store a plurality of the inner cabin images and the corresponding face detection results thereof, such as A data, B data, C data, and D data, etc, wherein the storing time of A data is the earliest and the storing order of other data is B data, C data, and D data in turn.

Figure 4:
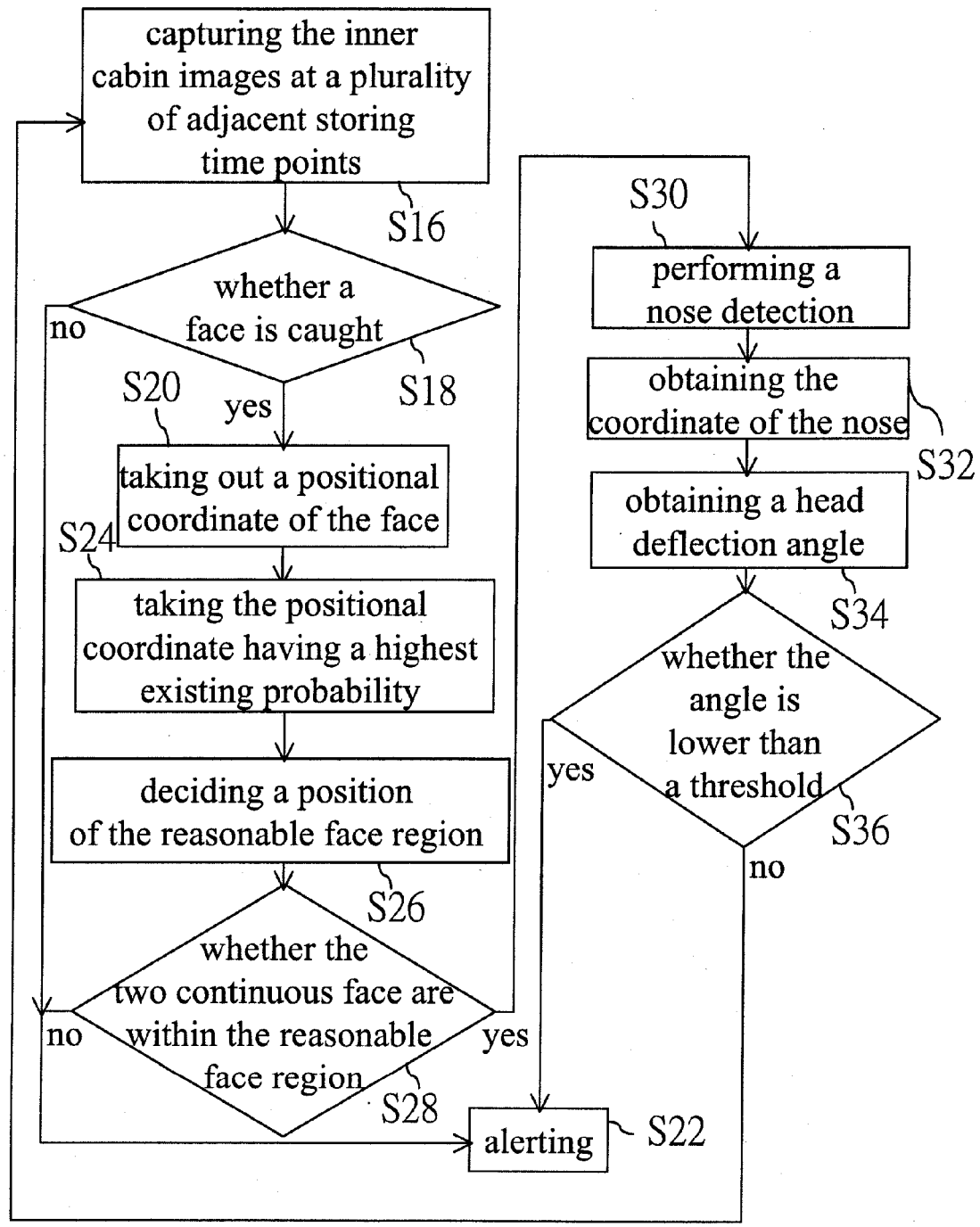
FIG. 4 is a flow chart of a determining method according to an embodiment of the present invention.

Refer to FIG. 1, FIG. 3 and FIG. 4. When the above-mentioned steps are performed completely, the control unit 14 counts an accumulating number of the inner cabin images stored in the memory 16. When the accumulating number has reached a predetermined value, a determining method is performed. Firstly, in Step S16, the control unit 14 captures the inner cabin images at a plurality of adjacent storing time points and the corresponding face detection results thereof. If the predetermined value is three, the data captured by the control unit 14 comprises A data, B data, and C data.

Next, in Step S18, the control unit 14 determines whether at least one of the corresponding inner cabin image catches the face of the driver according to each captured face detection result; if the answer is yes, the process proceeds to Step S20; if the answer is no, the process proceeds to Step S22. In Step S22, the control unit 14 outputs a control signal to the alerter 18 and then the alerter 18 outputs a warning signal to alert the driver.

In Step S20, the control unit 14 takes out the captured inner cabin images catching the face and the corresponding positional coordinate of the face thereof. Next, in Step S24, the control unit 14 analyzes the positional coordinate of the face of each captured inner cabin image, and then takes the positional coordinate of the face having the highest existing probability from the positional coordinate of the face of each captured inner cabin image. Next, in Step S26, the control unit 14 decides a position of the reasonable face region according to the positional coordinate having the highest existing probability used as a center coordinate of the reasonable face region.

Next, in Step S28, the control unit 14 determines whether the faces of the two continuous and corresponding inner cabin images are shown within the reasonable face region according to each captured face detection result; if the answer is yes, the process proceeds to Step S32; if the answer is no, the process proceeds to Step S22. In Step S22, the control unit 14 outputs the control signal to the alerter 18, and then the alerter 18 outputs the warning signal to alert the driver.

In Step S30, the image signal process unit 12 performs a nose detection of the driver on the presently-storing inner cabin image by an Adaboost algorithm. Next, in Step S32, the image signal process unit 12 obtains a positional coordinate of a nose of the driver. Next, in Step S34, the control unit 14 compares the positional coordinate of the nose with the reasonable face region to obtain a head deflection angle of the driver. Next, in Step S36, the control unit 14 determines whether the head deflection angle is lower than a predetermined threshold; if the answer is yes, the process proceeds to return to Step S16; if the answer is no, the process proceeds to Step S22.

When Step S16 is executed again, a part of the captured inner cabin images and the corresponding face detection results thereof are the same for the first time and the second time respectively. For instance, the captured data for the first time comprises A data, B data, and C data, and the captured data for the second time comprises B data, C data, and D data. In other words, the two data of B and C are the same for the first and second time.

Due to the distracting action of a driver is a continuous action, the present invention uses a time state sequence design to store the face detection results detected by an Adaboost algorithm in the past time sequence. Furthermore, the present invention uses the face detection results to analyze and identify the reasonable properties for the position of the face. This handling method can not only satisfy the continuous requirement of distracted driving but eliminate erroneous judgments due to the dispersed property of an Adaboost algorithm. Thus, the stability of the results outputted from the system is improved.

Step S20, Step S24 and Step S26 are called a reasonable face region correction process, and Step S30, Step S32 and Step S34 are called a nose detection process. One of the reasonable face region correction process and the nose detection process is omitted or the reasonable face region correction process and the nose detection process are both omitted, so as to achieve the purpose of monitoring the driver.

When the reasonable face region correction process is omitted, the control unit 14 predetermines a squarely-facing face region used as the reasonable face region. In Step S18, if the answer is yes, the process proceeds to Step S28. When the nose detection process is omitted and the determining result of Step S28 is yes, the process proceeds to return to Step S16. Moreover, the alerter 18 can improve the stability of the warning result by integrating outer driving environment signals (vehicle speed and direction light signal, etc.). For example, when movement of a car has stopped (a value of vehicle speed is zero), the system stops to operate. This is because a driver may be parking the car on a street. When a direction light signal of the car is sent out, the system is in a disable state. This is because the driver may want to turn light or left and a line of vision of the driver must be diverged from the front direction of the car. Furthermore, when a left direction light signal of the car is sent out, the control unit 14 determines whether a line of vision of the driver is towards the left direction; if the answer is yes, the system is in a normal state; if the line of vision of the driver is towards the right direction, the system sends out a warning signal to indicate that the driver isn't concentrating in the driving direction.

In conclusion, the present invention determines a driving state of a driver in a cabin with a method of analyzing a position of a face or a head and using an image extractor having a large capture range and a low resolution, so as to reduce the cost of the image extractor and improve the convenience for using the image extractor.

The embodiments described above are only to exemplify the present invention but not to limit the scope of the present invention. Therefore, any equivalent modification or variation according to the shape, structures, characteristics and spirit disclosed in the present invention is to be also included within the scope of the present invention.

What is claimed is:

1. A method for monitoring a driver comprising steps of:
    Step (A): capturing an inner cabin image of a cabin;
    Step (B): performing a face detection of the driver on said inner cabin image to obtain a face detection result;
    Step (C): storing said inner cabin image and said face detection result corresponding to said inner cabin image;
    Step (D): repeating said above-mentioned steps, and when an accumulated number of stored said inner cabin images reaches a predetermined value, executing steps of;
    Step (E): capturing said inner cabin images at a plurality of adjacent storing time points and corresponding said face detection results thereof;
    Step (F): determining whether at least one corresponding said inner cabin image catches a face of said driver according to each captured said face detection result;
    if no, outputting a warning signal to alert said driver; and
    if yes, executing a step of;
    Step (G): determining whether said faces of two continuous and corresponding said inner cabin images are shown within a reasonable face region according to each captured said face detection result to define a face region correction process; said face region correction process including taking a positional coordinate of the face, taking said positional coordinate having a highest existing probability, and deciding a position of said reasonable face region; and,
    (1) if said faces of two continuous and corresponding said inner cabin images are within said reasonable face region, then performing a nose detection of said driver on presently-stored said inner cabin image; obtaining a positional coordinate of a nose of said driver; comparing said positional coordinate of said nose with said reasonable face region to obtain a head deflection angle of said driver to define a nose detection process; determining whether said head deflection angle is lower than a predetermined threshold, and returning to said Step (E); and
    (2) if said faces of two continuous and corresponding said inner cabin images are not within said reasonable face region, then outputting said warning signal to alert said driver.

2. The method for monitoring a driver according to claim 1, wherein in said step of performing said face detection of said driver on said inner cabin image, an Adaboost algorithm is used to perform said face detection of said driver on said inner cabin image.

3. The method for monitoring a driver according to claim 1, wherein said reasonable face region is a predetermined region.

4. The method for monitoring a driver according to claim 1, wherein said reasonable face region is a squarely-facing face region.

5. The method for monitoring a driver according to claim 2, wherein said face detection result comprises a catch result and a positional coordinate of said face.

6. The method for monitoring a driver according to claim 5, wherein when a determination result of said Step (F) is yes and before said Step (G), said method further comprises steps of:
    taking out captured said inner cabin images catching said face and corresponding said positional coordinate of said face thereof;
    analyzing said positional coordinate of said face of each captured said inner cabin image and taking said positional coordinate having a highest existing probability from said positional coordinate of said face of each captured said inner cabin image as determined by said Adaboost algorithm; and
    deciding a position of said reasonable face region according to said positional coordinate having said highest existing probability.

7. The method for monitoring a driver according to claim 1, wherein said nose of said driver is detected by an Adaboost algorithm.

8. The method for monitoring a driver according to claim 1, wherein when said Step (E) is executed at two adjacent times, a part of captured said inner cabin images is equal.

9. A system for monitoring a driver comprising: an image extractor for continuously capturing an inner cabin image; an image signal process unit coupled to said image extractor for performing a face detection of the driver on said inner cabin image to obtain a face detection result;
    a control unit coupled to said image signal process unit and a memory, controlling to store said inner cabin image and corresponding said face detection result thereof in said memory, wherein when said control unit observes that a face is not shown in one said inner cabin image or said face is not shown within a reasonable face region of at least two continuous said inner cabin images according to each said face detection result stored in said memory, said control unit outputs a control signal, said control unit compares said positional coordinate of said nose with said reasonable face region to obtain a head deflection angle of said driver, and wherein when said control unit determines that a face is shown in one said inner cabin image according to said face detection result, said control unit takes a positional coordinate of the face and then takes said positional coordinate having a highest existing probability to decide a position of said reasonable face region; and an alerter for receiving said control signal and then outputting a warning signal to alert said driver said control unit controls said alerter to output said warning signal when said head deflection angle is higher than or equal to a predetermined threshold.

10. The system for monitoring a driver according to claim 9, wherein said image signal process unit performs said face detection of said driver on said inner cabin image by an Adaboost algorithm.

11. The system for monitoring a driver according to claim 9, wherein said reasonable face region is a predetermined region.

12. The system for monitoring a driver according to claim 9, wherein said reasonable face region is a squarely-facing face region.

13. The system for monitoring a driver according to claim 9, wherein said face detection result comprises a catch result and said positional coordinate of said face.

14. The system for monitoring a driver according to claim 13, wherein said control unit takes said inner cabin images catching said face from said memory according to each said face detection result stored in said memory, and said positional coordinate having said highest existing probability being determined by said Adaboost algorithm.

15. The system for monitoring a driver according to claim 9, wherein said control unit captures said inner cabin images and corresponding said face detection results thereof at a plurality of adjacent storing time points from said memory, and when said control unit observes that said face is not shown in one said inner cabin image or said face is not shown within said reasonable face region of at least two continuous said inner cabin images according to each captured said face detection result, said control unit outputs said control signal.

16. The system for monitoring a driver according to claim 9, wherein said nose of said driver is detected by an Adaboost algorithm.

17. The method for monitoring a driver according to claim 1, wherein said face detection result comprises a catch result and said positional coordinate of said face.

18. The system for monitoring a driver according to claim 9, wherein said face detection result comprises a catch result and said positional coordinate of said face.

* * * * *